(12) United States Patent
Chang et al.

(10) Patent No.: US 12,186,770 B2
(45) Date of Patent: Jan. 7, 2025

(54) DISINFECTION ROBOT

(71) Applicant: SOUTHWEST JIAOTONG UNIVERSITY, Chengdu (CN)

(72) Inventors: Xianghui Chang, Chengdu (CN); Yajing Cui, Chengdu (CN); Qijun Liu, Chengdu (CN); Xia Liu, Chengdu (CN); Weidong Qiu, Chengdu (CN); Yan Yan, Chengdu (CN); Wenguang Li, Chengdu (CN)

(73) Assignee: SOUTHWEST JIAOTONG UNIVERSITY, Chengdu (CN)

( * ) Notice: Subject to any disclaimer, the term of this patent is extended or adjusted under 35 U.S.C. 154(b) by 0 days.

(21) Appl. No.: 18/757,491

(22) Filed: Jun. 27, 2024

(65) Prior Publication Data
US 2024/0342741 A1 Oct. 17, 2024

Related U.S. Application Data

(63) Continuation of application No. PCT/CN2023/103149, filed on Jun. 28, 2023.

(30) Foreign Application Priority Data

Aug. 4, 2022 (CN) .......................... 202210943832.1

(51) Int. Cl.
| | |
|---|---|
| *B05B 13/04* | (2006.01) |
| *A61L 2/18* | (2006.01) |
| *A61L 2/26* | (2006.01) |
| *B05B 15/25* | (2018.01) |
| *G05D 1/689* | (2024.01) |
| *G05D 105/10* | (2024.01) |

(52) U.S. Cl.
CPC ............ *B05B 13/0431* (2013.01); *A61L 2/18* (2013.01); *A61L 2/26* (2013.01); *B05B 15/25* (2018.02); *A61L 2202/15* (2013.01); *A61L 2202/16* (2013.01); *A61L 2202/25* (2013.01); *G05D 1/6895* (2024.01); *G05D 2105/10* (2024.01)

(58) Field of Classification Search
CPC ....... B05B 13/0431; B05B 15/25; A61L 2/18; A61L 2/26; A61L 2202/15; A61L 2202/16; A61L 2202/25; G05D 1/6895; G05D 2105/10
USPC ................ 239/263.1, 263.3, 264, 587.1, 588
See application file for complete search history.

(56) References Cited

FOREIGN PATENT DOCUMENTS

| | | | |
|---|---|---|---|
| CN | 104960566 | A | 10/2015 |
| CN | 108575878 | A | 9/2018 |
| CN | 108855707 | A | 11/2018 |
| CN | 108970844 | A | 12/2018 |
| CN | 209221068 | U | 8/2019 |

(Continued)

*Primary Examiner* — Christopher S Kim

(57) ABSTRACT

A disinfection robot, including a top plate, a bottom plate and a swinging mechanism. The top plate is located above the bottom plate. The swinging mechanism is located between the top plate and the bottom plate, and includes a swinging arm, a hinge shaft, a swinging gear, two swinging units and a driving unit. The swinging arm is hingedly connected to the bottom plate through the hinge shaft. The two swinging units are symmetrically arranged on both sides of the swinging gear. Each of the two swinging units includes a swinging shaft, an incomplete gear and a linear driver. The driving unit is configured to simultaneously drive swinging shafts of the two swinging units to rotate in opposite directions. The disinfection robot can adjust a swing amplitude of the swinging arm according to a size of a disinfection site.

10 Claims, 8 Drawing Sheets

(56) References Cited

FOREIGN PATENT DOCUMENTS

| | | |
|---|---|---|
| CN | 112754884 A | 5/2021 |
| CN | 112808728 A | 5/2021 |
| CN | 213102887 U | 5/2021 |
| CN | 213789053 U | 7/2021 |
| CN | 113842482 A | 12/2021 |
| CN | 216169023 U | 4/2022 |
| CN | 216536316 U | 5/2022 |
| CN | 216676457 U | 6/2022 |
| CN | 115350300 A | 11/2022 |
| JP | H07127701 A | 5/1995 |
| JP | 2001009335 A | 1/2001 |
| JP | 2003181346 A | 7/2003 |
| JP | 2006167667 A | 6/2006 |
| WO | 2022007539 A1 | 1/2022 |

DISINFECTION ROBOT

CROSS-REFERENCE TO RELATED APPLICATIONS

This application is a continuation of International Patent Application No. PCT/CN2023/103149, filed on Jun. 28, 2023, which claims the benefit of priority from Chinese Patent Application No. 202210943832.1, filed on Aug. 4, 2022. The content of the aforementioned application, including any intervening amendments made thereto, is incorporated herein by reference in its entirety.

TECHNICAL FIELD

This application relates to disinfection devices, and more particularly to a disinfection robot.

BACKGROUND

The environmental sanitation of high-speed trains has become increasingly severe due to the novel coronavirus, posing a challenge to the environmental problems in the carriages. The presence of viruses in the carriages is directly related to human health. Therefore, how to efficiently disinfect the carriages of high-speed trains, especially the pedestrian walkways inside the carriages, is an urgent problem to be solved.

At present, most of the disinfection methods for the pedestrian walkways inside the carriages still adopt traditional manual spraying disinfection. The entire disinfection process is completed manually, resulting in a high labor intensity and a low disinfection efficiency. With the development of science and technology, disinfection robots that can automatically disinfect have appeared. Such disinfection robots can walk and spray disinfectant autonomously to replace manual disinfection of the ground such as the pedestrian walkway in the carriage. The entire disinfection process does not require human intervention, which greatly improves the disinfection efficiency.

However, conventional disinfection robots are commonly provided with fixed spray nozzles, such that the spraying range of the spray nozzle is fixed, and the size of the spraying range cannot be adjusted according to the size of the actual disinfection site. On this basis, some disinfection robots with swingable spray nozzles to expand the spraying range thereof have appeared. For example, Chinese Patent No. 216169023U discloses a swing-type atomizing disinfection robot. A spray nozzle of such disinfection robot is arranged on a swinging arm capable of swinging back and forth, such that the spray nozzle is driven by the swinging arm to swing, thereby expanding the spraying range of the spray nozzle. However, for the above disinfection robot, the spraying range of the spray nozzle can be extended by swinging, but still fixed, namely, the swing amplitude of the spray nozzle cannot be adjusted as needed, such that it cannot adapt to to-be-disinfected sites varying in area, and the practical application is limited to some extent.

SUMMARY

An object of the disclosure is to provide a disinfection robot, so as to at least overcome the technical problems in the prior art that it fails to adjust a swing amplitude of a spray nozzle according to a size of a disinfection site.

In order to achieve the above object, the following technical solutions are adopted.

This application provides a disinfection robot, comprising:
a top plate;
a bottom plate;
a swinging mechanism; and
a spraying mechanism;
wherein the top plate is located above the bottom plate; and the swinging mechanism is located between the top plate and the bottom plate;
the swinging mechanism comprises a swinging arm, a hinge shaft, a swinging gear, a first swinging unit, a second swinging unit and a driving unit;
the swinging arm has a first end and a second end;
the swinging arm is hingedly connected to the bottom plate through the hinge shaft with a hinge position located between the first end and the second end of the swinging arm;
the swinging gear is sleevedly arranged on an outer wall of the hinge shaft, and is coaxially arranged with the hinge shaft;
the first swinging unit is arranged at a first side of the swinging gear, and the second swinging unit is arranged at a second side of the swinging gear; the first swinging unit is symmetrically arranged with the second swinging unit; each of the first swinging unit and the second swinging unit comprises a swinging shaft, an incomplete gear and a linear driver; the swinging shaft is freely rotatable, and is vertically arranged; the incomplete gear comprises a rotating portion and a plurality of tooth portions; the rotating portion is sleevedly arranged on an outer wall of the swinging shaft, and is slidable along an axial direction of the swinging shaft; the plurality of tooth portions are sequentially arranged on a circumferential outer wall of the rotating portion from top to bottom; each of the plurality of tooth portions comprises a plurality of teeth sequentially provided along a circumferential direction of the rotating portion; the plurality of tooth portions vary in the number of the plurality of teeth, and are configured to be respectively engaged with the swinging gear; the linear driver is coaxially rotatable with the swinging shaft; and an output end of the linear driver is connected to the rotating portion to drive the rotating portion to slide along the axial direction of the swinging shaft; and
the driving unit is configured to simultaneously drive the swinging shaft of the first swinging unit and the swinging shaft of the second swinging unit to rotate in opposite directions, such that the incomplete gear of the first swinging unit and the incomplete gear of the second swinging unit are alternately engaged with the swinging gear.

In some embodiments, the spraying mechanism comprises a liquid storage tank having a liquid storage cavity, a spray nozzle and a liquid pump; the liquid storage tank is arranged on a top of the top plate; the spray nozzle is arranged at the first end of the swinging arm; an input end of the liquid pump is connected to the liquid storage cavity through a pipeline; and an output end of the liquid pump is connected to the spray nozzle through a hose.

In some embodiments, the spraying mechanism further comprises a stirring blade; a top end of the swinging shaft of the first swinging unit passes through the top plate and the liquid storage tank in sequence to extend into the liquid storage cavity; and the stirring blade is arranged on the outer wall of the swinging shaft of the first swinging unit, and is located inside the liquid storage cavity.

In some embodiments, the spraying mechanism further comprises a damping shaft; and the spray nozzle is rotatably connected to the first end of the swinging arm through the damping shaft.

In some embodiments, a top of the liquid storage tank has an open structure, and is threadedly connected to a cover; and the stirring blade is arranged in plurality; and a plurality of stirring blades are sequentially provided along the axial direction of the swinging shaft of the first swinging unit.

In some embodiments, the driving unit comprises a driving motor and two transmitting gears; the driving motor is arranged on the top plate; an output end of the driving motor is in transmission connection with the swinging shaft of one of the first swinging unit and the second swinging unit; one of the two transmitting gears is sleevedly arranged on the outer wall of the swinging shaft of the first swinging unit, and is coaxially rotatable with the swinging shaft of the first swinging unit, and the other of the two transmitting gears is sleevedly arranged on the outer wall of the swinging shaft of the second swinging unit, and is coaxially rotatable with the swinging shaft of the second swinging unit; the two transmitting gears are engaged with each other; and the linear driver is fixedly arranged at a bottom of a corresponding one of the two transmitting gears.

In some embodiments, the disinfection robot further comprises a liquid spreading mechanism; wherein the liquid spreading mechanism comprises a liquid spreading head arranged at the second end of the swinging arm; and a bottom of the liquid spreading head is provided with a plurality of bristles.

In some embodiments, the liquid spreading mechanism further comprises a liquid spreading shaft, a liquid spreading gear and a liquid spreading gear ring; the liquid spreading head is rotatably connected to the second end of the swinging arm through the liquid spreading shaft; the liquid spreading gear is sleevedly arranged on an outer wall of the liquid spreading shaft, and is coaxially arranged with the liquid spreading shaft; the liquid spreading gear ring has an arc-shaped structure, and is adapted to fit a swinging path of the swinging arm; and the liquid spreading gear is engaged with the liquid spreading gear ring.

In some embodiments, the disinfection robot further comprises a guard plate; the guard plate has an annular closed structure, and a space enclosed by the guard plate is configured as a protecting cavity; the swinging mechanism is located in the protecting cavity; two opposite sides of the guard plate are each provided with an avoidance opening; and the first end and the second end of the swinging arm extend outside the protecting cavity through avoidance openings on the two opposite sides of the guard plate, respectively.

In some embodiments, the hinge position is located at a center of the swinging arm.

In some embodiments, two opposite sides of a top of the bottom plate are each provided with a sliding groove in an arc shape; two opposite sides of a bottom of the swinging arm are each provided with a sliding column fitting the sliding groove; one of sliding columns is located between the hinge shaft and the first end of the swinging arm; and the other of the sliding columns is located between the hinge shaft and the second end of the swinging arm.

Compared to the prior art, the present disclosure has the following beneficial effects:

1. By virtue of the further improvement of a structure of the swinging mechanism based on the prior art, the disinfection robot can adjust a swing amplitude of the swinging arm according to the size of the disinfection site, thereby adjusting the spraying range of the spray nozzle, so as to improve the practicality of the disinfection robot. This facilitates the disinfection of disinfection sites with virous sizes, resulting in a better use effect and a higher disinfection efficiency.
2. For the disinfection robot provided herein, a stirring blade is provided on the swinging shaft of the first swinging unit, such that a disinfectant and a drug in the liquid storage cavity can be fully stirred and mixed by the stirring blade, thereby further improving the disinfection effect. Furthermore, A driving motor is provided to simultaneously realize the swing of the swinging arm and the rotation of the stirring blade, leading to a more rational use of resources. In addition, the reciprocating swing of the swinging arm can be realized by using an ordinary motor as the driving motor, without using a servo motor or a stepper motor with a higher cost.
3. The disinfection robot is provided with the liquid spreading mechanism, such that the liquid spreading head and the bristles thereof can be used to spread the disinfectant sprayed onto ground by the spray nozzle. This can effectively avoid the accumulation of a large amount of disinfectant in a local area on the ground, such that the disinfectant can be more evenly distributed on the ground of the disinfection site.

Figure 1:
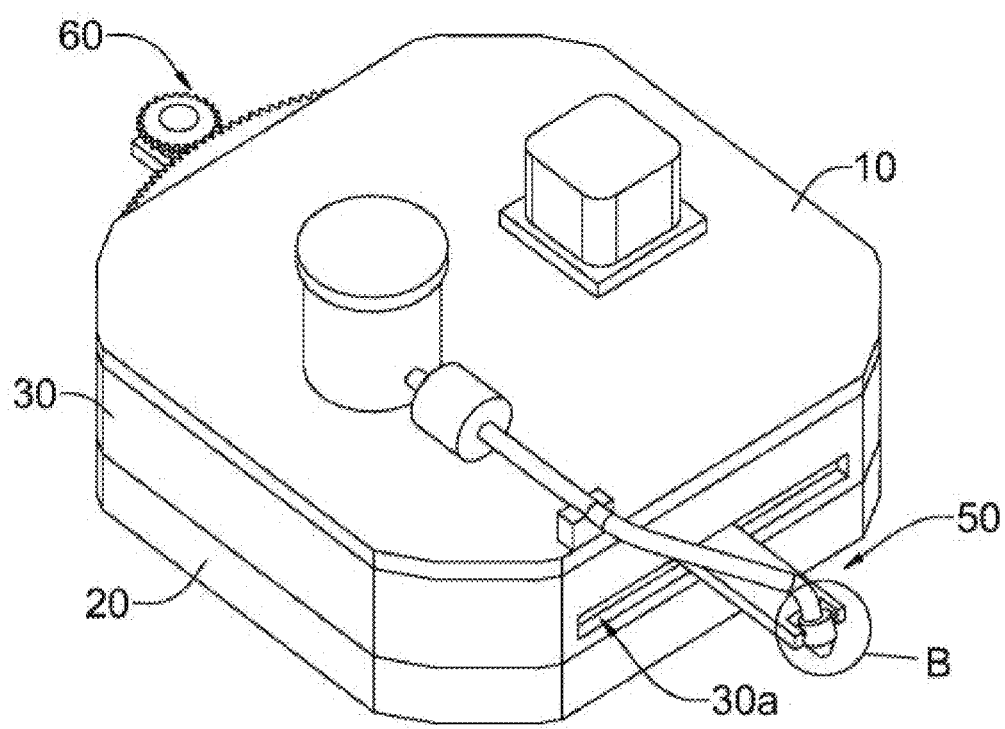
FIG. 1 is a structural diagram of a disinfection robot in accordance with an embodiment of the present disclosure.

In the drawings: 10—top plate; 20—bottom plate; 20a—sliding groove; 30—guard plate; 30a—avoidance opening; 40—swinging mechanism; 41—swinging arm; 42—hinge shaft; 43—swinging gear; 44—swinging unit; 441—swinging shaft; 442—incomplete gear; 4421—rotating portion; 4422—tooth portion; 4422a—tooth; 443—linear driver; 45—driving unit; 451—driving motor; 452—transmitting gear; 46—sliding column; 50—spraying mechanism; 51—liquid storage tank; 52—spray nozzle; 53—liquid pump; 54—cover; 55—damping shaft; 56—stirring blade; 60—liquid spreading mechanism; 61—liquid spreading head; 62—liquid spreading shaft; 63—liquid spreading gear; and 64—liquid spreading gear ring.

DETAILED DESCRIPTION OF EMBODIMENTS

As shown in FIGS. 1-8, a disinfection robot is provided, including a top plate 10, a bottom plate 20, a guard plate 30, a swinging mechanism 40, a spraying mechanism 50 and a liquid spreading mechanism 60.

Figure 2:
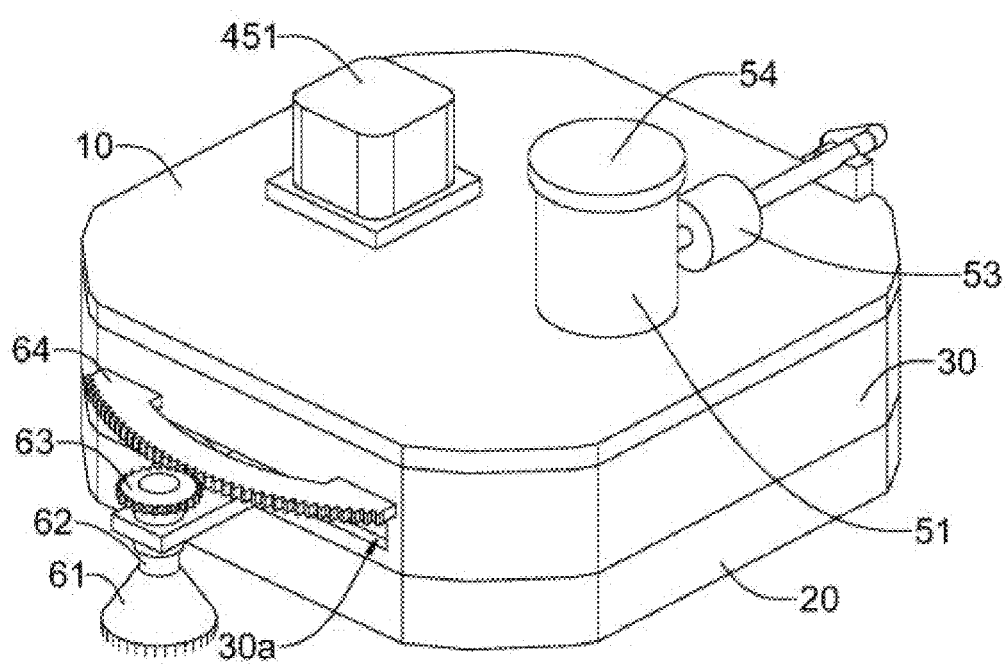
FIG. 2 is a structural diagram of the disinfection robot in accordance with an embodiment of the present disclosure from another angle of view.
Figure 3:
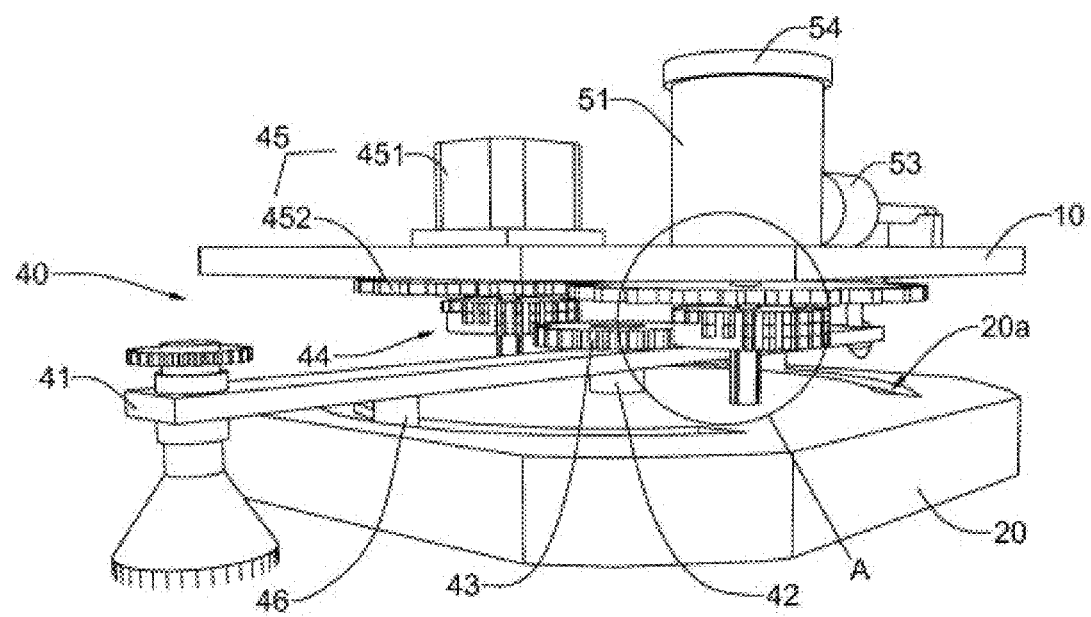
FIG. 3 schematically shows an internal structure of the disinfection robot in accordance with an embodiment of the present disclosure.

In this embodiment, referring to FIGS. 1-3, the top plate 10 is located above the bottom plate 20. The guard plate 30 is arranged on a top of the bottom plate 20, and has an annular closed structure. An upper side of the guard plate 30 is connected to the top plate 10. A lower side of the guard plate 30 is connected to the bottom plate 20. In this way, the top plate 10, the bottom plate 20 and the guard plate 30 are configured as a main support structure of the disinfection robot, and enclose a relatively closed protecting cavity to protect various components arranged inside the protecting cavity. In addition, a moving mechanism composed of moving wheels (not shown in the drawings) is provided at a bottom of the bottom plate 20, such that the disinfection robot can walk autonomously, so as to disinfect the ground of a disinfection site through the continuous movement of the disinfection robot. A specific structure of the moving mechanism can refer to a structure of a moving mechanism in the prior art. The moving mechanism will not be described in detail due to its unimproved structure.

In this embodiment, referring to FIG. 3, the swinging mechanism 40 is located between the top plate 10 and the bottom plate 20. Specifically, the swinging mechanism 40 is located in the protecting cavity formed by the top plate 10, the bottom plate 20 and the guard plate 30, so as to protect various components of the swinging mechanism 40.

Referring to FIG. 3, the swinging mechanism 40 includes a swinging arm 41, a hinge shaft 42, a swinging gear 43, two swinging units 44 and a driving unit 45. The swinging arm 41 has a first end and a second end. The swinging arm 41 is hingedly connected to the bottom plate 20 through the hinge shaft 42 with a hinge position located between the first end and the second end of the swinging arm 41, such that the swinging arm 41 can perform a reciprocating circular motion with the hinge shaft 42 as a center, thereby realizing the reciprocating swing of the swinging arm 41. At this time, the first end and the second end of the swinging arm 41 are both configured as swinging ends. In addition, the first end of the swinging arm 41 is commonly configured as a front end of the disinfection robot during movement.

It can be understood that, in practical implementation, the hinge position can be located at a center of the swinging arm 41, such that during the reciprocating swing of the swinging arm 41, the first end and the second end of the swinging arm 41 have the same swing amplitude (that is, the first end and the second end of the swinging arm 41 have the same swing stroke). Moreover, referring to FIGS. 3 and 6, two opposite sides of the top of the bottom plate 20 are each provided with a sliding groove 20a in an arc shape. The sliding groove 20a is adapted to fit a swinging path of the swinging arm 41. Two opposite sides of a bottom of the swinging arm 41 are each provided with a sliding column 46 fitting the sliding groove 20a. One of the sliding columns 46 is located between the hinge shaft 42 and the first end of the swinging arm 41. The other of the sliding columns 46 is located between the hinge shaft 42 and the second end of the swinging arm 41. When the swinging arm 41 swings, the two sliding columns 46 at the bottom of the swinging arm 41 can respectively slide in the corresponding sliding grooves 20a to further improve the stability of the swinging arm 41 during a swinging process.

Correspondingly, referring to FIGS. 1-2, two opposite sides of the guard plate 30 are each provided with an avoidance opening 30a. The first end and the second end of the swinging arm 41 extend outside the protecting cavity through the avoidance openings 30a on the two opposite sides of the guard plate 30, respectively, so as to enable the swinging arm 41 smoothly perform reciprocating swing and to avoid interference between the swinging arm 41 and the guard plate 30 during the swinging process.

Referring to FIG. 3, the swinging gear 43 is sleevedly arranged on an outer wall of the hinge shaft 42, and is coaxially arranged with the hinge shaft 42, such that the swinging gear 43 is coaxially rotatable with the hinge shaft 42. The two swinging units 44 are symmetrically arranged on both sides of the swinging gear 43, such that the swinging gear 43 can be driven by the two swinging units 44 to rotate reciprocatingly within a certain angle range, thereby allowing the swinging gear 43 to drive the hinge shaft 42 to rotate reciprocatingly. In this way, the swinging arm 41 can swing reciprocatingly within the certain angle range under the action of the hinge shaft 42 rotating reciprocatingly.

Figure 4:
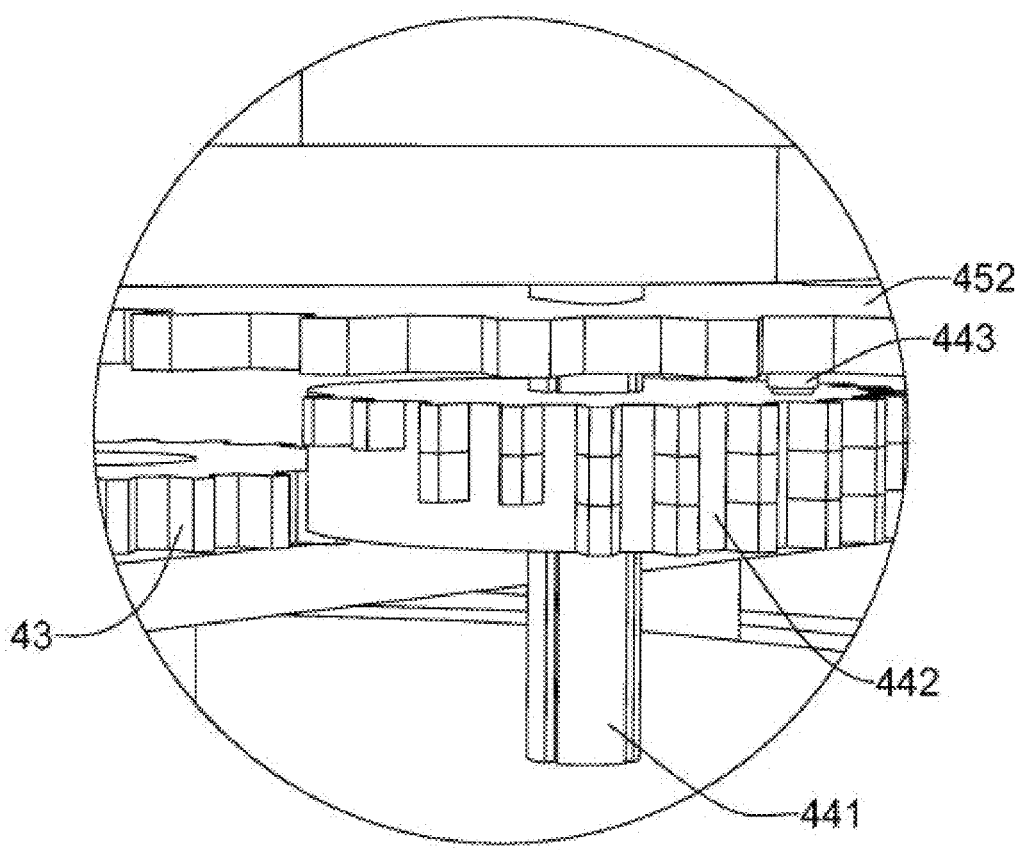
FIG. 4 is an enlarged view of part A in FIG. 3.
Figure 5:
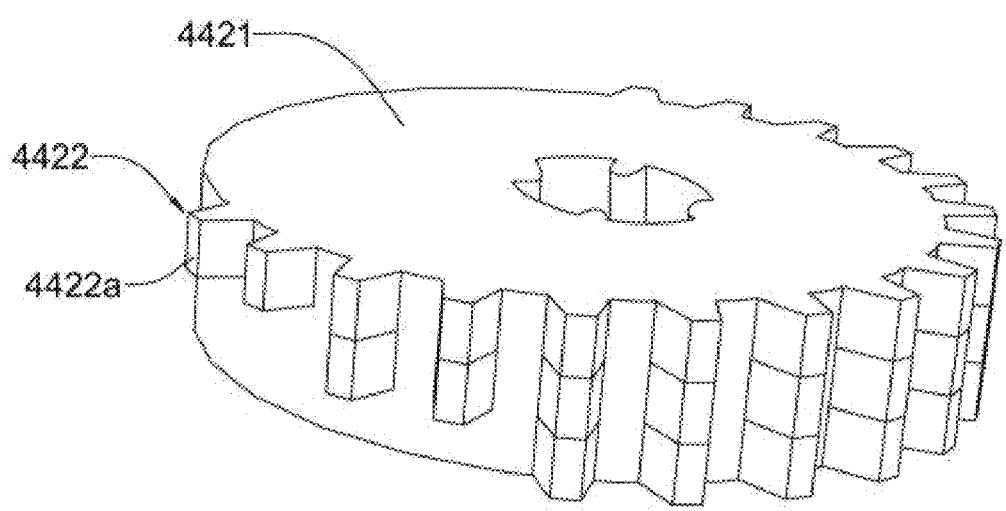
FIG. 5 is a structural diagram of an incomplete gear of a swinging unit in accordance with an embodiment of the present disclosure.
Figure 6:
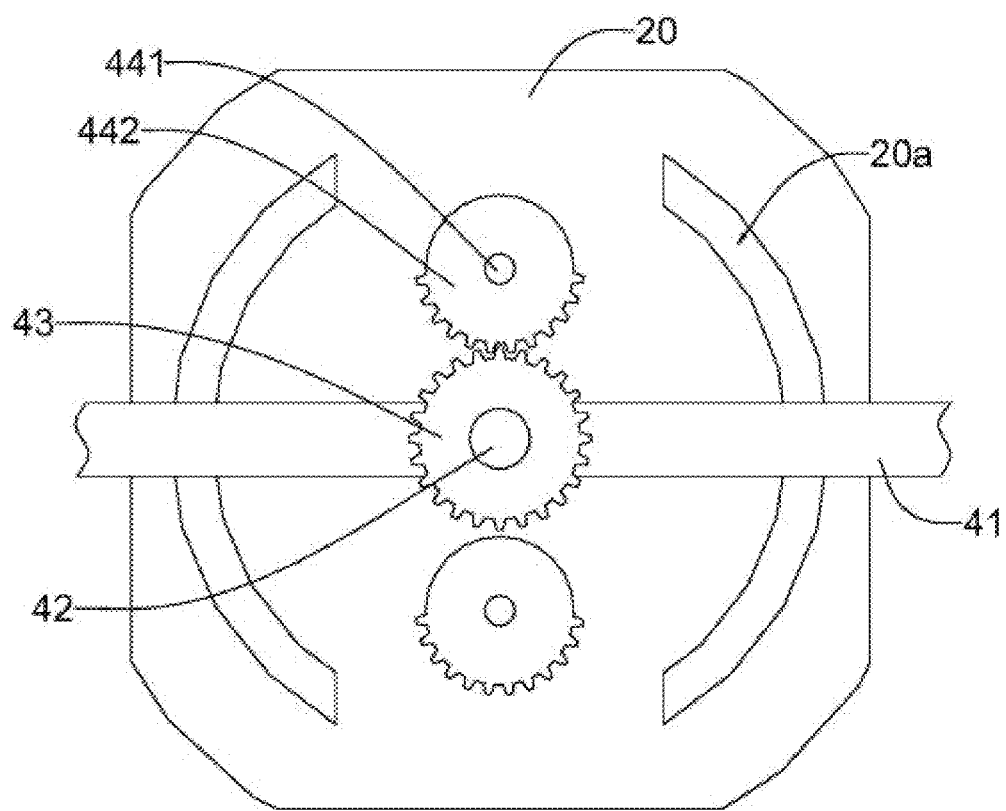
FIG. 6 is a top view of a bottom plate and a partial structure of a swinging mechanism in accordance with an embodiment of the present disclosure.

In order to achieve various swing amplitudes for the swinging arm 41, specifically, referring to FIGS. 4 and 6, each of the two swinging units 44 includes a swinging shaft 441, an incomplete gear 442 and a linear driver 443. The swinging shaft 441 is freely rotatable, and is vertically arranged. In an embodiment, a bottom end of the swinging shaft 441 of each of the two swinging units 44 is rotatably connected to the top of the bottom plate 20 to improve the stability of the swinging shaft 441 during the rotation process. Referring to FIG. 5, the incomplete gear 442 includes a rotating portion 4421 and a plurality of tooth portions 4422. The rotating portion 4421 is slidably and sleevedly arranged on an outer wall of the swinging shaft 441, and is coaxially arranged with the swinging shaft 441, such that the rotating portion 4421 can simultaneously slide along the axial direction of the swinging shaft 441 and rotate synchronously with the swinging shaft 441. It can be understood that, referring to FIG. 4, in practical implementation, a plurality of limit grooves extending along the axial direction of the swinging shaft 441 can be can be provided on the outer wall of the swinging shaft 441 of each of the two swing units 44. The plurality of limit grooves are arranged in sequence along a circumferential direction of the swinging shaft 441. The rotating portion 4421 is partially located in a corresponding limit groove, and is slidable along the limit groove, so as to play a limiting and guiding role through the limiting groove, thereby improving the stability of the rotating portion 4421 when sliding along the axial direction of the swinging shaft 441.

Referring to FIG. 5, the plurality of tooth portions 4422 are sequentially arranged on a circumferential outer wall of the rotating portion 4421 from top to bottom. Each of the plurality of tooth portions 4422 includes a plurality of teeth 4422a sequentially provided along a circumferential direction of the rotating portion 4421. The plurality of tooth portions 4422 vary in the number of the plurality of teeth 4422a. The plurality of tooth portions 4422 are configured to be respectively engaged with the swinging gear 43, that is, when the rotating portion 4421 slides along the axial direction of the swinging shaft 441, the plurality of tooth portions 4422 can be engaged with the swinging gear 43 respectively. In this way, based on the different numbers of teeth 4422a of each of the plurality of tooth portions 4422, when the plurality of tooth portions 4422 varying in the number of the plurality of teeth 4422a are respectively engaged with the swinging gear 43, the incomplete gear 442 is driven by the swinging shaft 441 to rotate with each rotation leading to a different rotation angle of the swinging gear 43. It can be understood that the plurality of tooth portions 4422 of the incomplete gear 442 and the rotating portion 4421 are an integrated structure, so as to ensure the integrity of a structure of the incomplete gear 442.

Referring to FIG. 4, the linear driver 443 is coaxially rotatable with the swinging shaft 441. An output end of the linear driver 443 extends along a vertical direction to be connected to a top of the rotating portion 4421, such that the rotating portion 4421 is driven by the linear driver 443 to slide reciprocatingly along the axial direction of the swinging shaft 441, thereby enabling the plurality of tooth portions 4422 varying in the number of the plurality of teeth 4422a to be respectively engaged with the swinging gear 43. It can be understood that the linear driver 443 can be but is not limited to an electric push rod with a small volume. In this case, a free end of a piston rod of the electric push rod extends along a vertical direction to be connected to the top of the rotating portion 4421.

The driving unit 45 is configured to simultaneously drive the swinging shafts of the two swinging units 44 to rotate in opposite directions, thereby allowing the two swinging units 441 to drive the swinging gear 43 to rotate reciprocatingly within a certain angle range.

Specifically, referring to FIG. 6, in an initial state, the incomplete gears 442 of the two swinging units 44 are at the same height, and tooth portions 4422 with the same number of teeth 4422a on the incomplete gears 442 of the two swinging units 44 respectively correspond to the swinging gear 43. In this case, the plurality of tooth portions 4422 corresponding to the incomplete gear 442 of one of the two swinging units 44 are engaged with the swinging gear 43, while tooth portions 4422 corresponding to the incomplete gear 442 of the other of the two swinging units 44 are not engaged with the swinging gear 43. When the swinging shafts 441 of the two swinging units 44 are driven by the driving unit 45 to rotate in opposite directions, the tooth portions 4422 of the incomplete gears 442 of the two swinging units 44 can be alternately engaged with the swinging gear 43. In other words, based on the fact that the plurality of tooth portions 4422 of the incomplete gear 442 of one of the two swinging units 44 are engaged with the swinging gear 43 in the initial state, when the swinging shaft 441 of this swinging unit 44 is driven by the driving unit 45 to rotate, the swinging gear 43 will rotate a certain angle under the action of the incomplete gear 442 of this swinging unit 44, such that the hinge shaft 42 is driven by the swinging gear 43 to rotate a certain angle, so as to enable the hinge shaft 42 to drive the swinging arm 41 to swing a certain angle. When the plurality of tooth portions 4422 of the incomplete gear 442 of this swinging unit 44 rotates to disengage from the swinging gear 43, the incomplete gear 442 of the other swinging unit 44 can rotate until its tooth portions 4422 are engaged with the swinging gear 43. Since the swinging shaft 441 of such swinging unit 44 rotates in the opposite direction, as the swinging shaft 441 of such swing unit 44 rotates, the swinging gear 43 will rotate in the opposite direction by a certain angle under the action of the incomplete gear 442 of such swinging unit 44, thereby realizing the reverse swing of the swinging arm 41 by a certain angle. In other words, each rotation of the swinging shafts 441 of the two swinging units 44 driven by the driving unit 45 leads to the swinging arm 41 swinging forward and reverse once within a certain angle range. When the swinging shafts 441 of the two swinging units 44 continuously rotate, the swinging arm can continuously perform reciprocating swing within the certain angle range.

It can be understood that the more teeth 4422a of a tooth portion 4422, the greater the angle at which the swinging gear 43 is driven to rotate per rotation of the incomplete gear 442. Conversely, the fewer teeth 4422a of a tooth portion 4422, the smaller the angle at which the swinging gear 43 is driven to rotate per rotation of the incomplete gear 442. Therefore, when the swing amplitude of the swinging arm 41 needs to be changed, it is only needed to utilize the linear drivers 443 of the two swinging units 44 to simultaneously drive the rotating portions of the corresponding incomplete gears 442 to slide along the axial direction of the corresponding swinging shafts 441, so as to allow the plurality of tooth portions varying in the number of the teeth 4422a to correspond to the swinging gear 43. For example, referring to FIG. 5, in this embodiment, the incomplete gear 442 of each of the two swinging units 44 has three tooth portions 4422. The number of teeth 4422a of the three tooth portions 4422 decreases from top to bottom. When a bottom tooth portion 4422 corresponds to the swinging gear 43, the swinging arm 41 has the smallest swing amplitude. When a top tooth portion 4422 corresponds to the swinging gear 43, the swinging arm 41 has the largest swing amplitude.

In this embodiment, referring to FIG. 3, the driving unit 45 includes a driving motor 451 and two transmitting gears 452. The driving motor 451 can be fixedly arranged on a top of the top plate 10. A top end of the swinging shaft 441 of a corresponding one of the two swinging units 44 passes through the top plate 10 to be transmission-connected to an output end of the driving motor 451, such that the swinging shaft 441 of the corresponding one of the two swinging units 44 is driven by the driving motor 451 to rotate. The two transmitting gears 452 are respectively sleevedly arranged on outer walls of the swinging shafts 441 of the two swinging units 44, and are respectively coaxially rotatable with corresponding swinging shafts 441. Moreover, the two transmitting gears 452 are engaged with each other. In this way, when the swinging shaft 441 of the corresponding one of the two swinging units 44 is driven by the driving motor 451 to rotate, a corresponding transmitting gear 452 can rotate synchronously with this swinging shaft 441, such that the other transmitting gear 452 is driven by the corresponding transmitting gear 452 to rotate in a opposite direction so as to realize the reverse rotation of the swinging shaft 441 of the other of the two swinging units 44.

It can be understood that, referring to FIG. 4, the linear driver 443 of each of the two swinging units 44 can be fixedly arranged at a bottom of a corresponding one of the two transmitting gears 452, such that the linear driver 443 can rotate coaxially with a corresponding swinging shaft 441. This can avoid interference between the linear driver 443 and the rotating portion 4421 during the rotation of the incomplete gear 442, such that the rotating portion 4421 can be smoothly driven by the linear driver 443 to slide along the axial direction of the swinging shaft 441 when appropriate.

In this embodiment, the spraying mechanism 50 is configured to spray a disinfectant onto a ground of a to-be-disinfected site, so as to realize the disinfection of the ground of the to-be-disinfected site. Specifically, referring to FIGS. 2-3, the spraying mechanism 50 includes a liquid storage tank 51 having a liquid storage cavity, a spray nozzle 52 and a liquid pump 53. The liquid storage tank 51 is arranged on the top of the top plate 10 for storing the disinfectant. It can be understood that, in order to facilitate adding the disinfectant into the liquid storage cavity, a top of the liquid storage tank 51 has an open structure, and is provided with a cover 54 for sealing the open structure. When the disinfectant needs to be added to the liquid storage cavity, it is only needed to remove the cover 54. In an embodiment, the cover 54 is threadedly connected to the liquid storage tank 51 to facilitate the disassembly and assembly of the cover 54.

Figure 7:
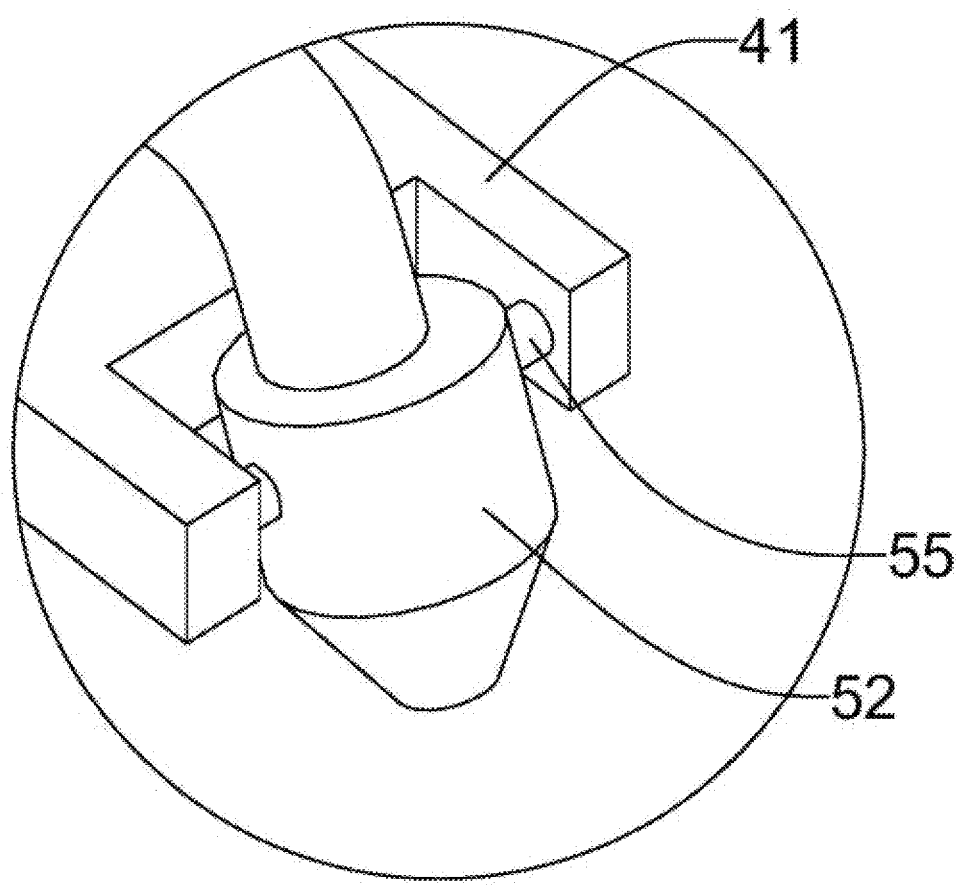
FIG. 7 is an enlarged view of part B in FIG. 1.

Referring to FIG. 7, the spray nozzle 52 is arranged at the first end of the swinging arm 41. It should be noted that the spraying mechanism 50 further includes a damping shaft 55. Moreover, the spray nozzle 52 is rotatably connected to the first end of the swinging arm 41 through the damping shaft 55, so as to facilitate the adjustment of a spray angle of the spray nozzle 52 as needed. Since the damping shaft 55 is configured as a hinging component, the spray nozzle 52 can be rotated to any angle and then stopped. The liquid pump 53 is configured to enable the disinfectant in the liquid storage tank 51 to be pumped to the spray nozzle 52 and subsequently sprayed out. Referring to FIGS. 2-3, the liquid pump 53 is arranged on the top of the top plate 10. An input end of the liquid pump 53 is connected to the liquid storage cavity through a pipeline. An output end of the liquid pump 53 is connected to the spray nozzle 52 through a hose. The hose is configured for the connection of the liquid pump 53 to the spray nozzle 52, and has a sufficient length to avoid interference between the spray nozzle 52 and the liquid pump 53 when the spray nozzle 52 is driven by the swinging arm to swing.

On the other hand, in practical application, the disinfectant is commonly added with some solid drugs. Such drugs are directly added to the disinfectant, resulting in a slow melting process, which is not conducive to the full mixing of the drugs and the disinfectant. On this basis, a stirring assembly for stirring the disinfectant in the liquid storage tank 51 is further provided. Specifically, referring to FIG. 8, the spraying mechanism 50 further includes a stirring blade 56. A top end of the swinging shaft 441 of a corresponding one of the two swinging units 44 passes through the top plate 10 and the liquid storage tank 51 in sequence to vertically extend into the liquid storage cavity. The swinging shaft 441 of the corresponding one of the two swinging units 44 is rotatably sealed and connected to the liquid storage tank 51 to prevent the disinfectant from leaking from a connection between the liquid storage tank 51 and the swinging shaft 441. In an embodiment, the swinging unit 44 corresponding to the swinging shaft 441 extending into the liquid storage tank 51 is not the swinging unit 44 corresponding to the swinging shaft 441 transmission-connected to the drive motor 451, that is, the swinging shaft 441 of one of the two swinging units 44 is transmission-connected to the drive motor 451, and the swinging shaft 441 of the other of the two swinging units 44 extends vertically into the liquid storage cavity, leading to a more reasonable structural design of the disinfection robot.

Figure 8:
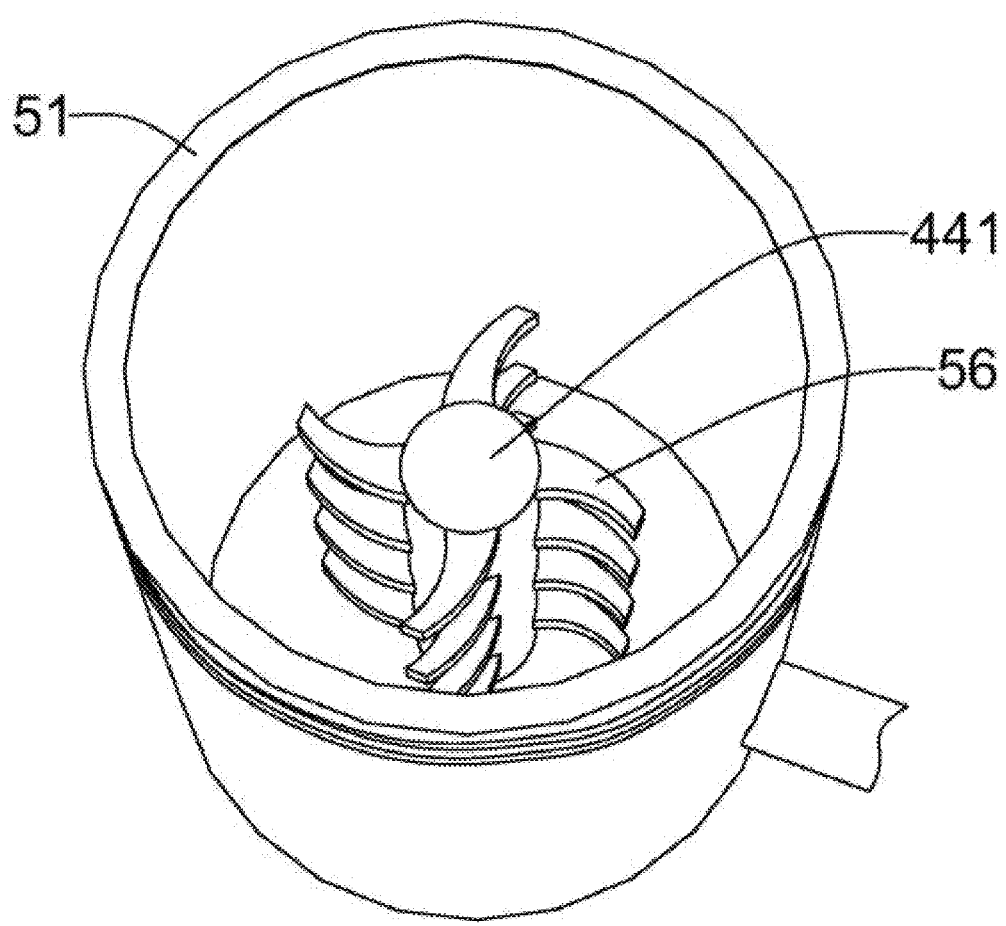
FIG. 8 is a schematic diagram of an internal structure of a liquid storage tank in accordance with an embodiment of the present disclosure.

Referring to FIG. 8, the stirring blade 56 is arranged on the outer wall of the swinging shaft 441 of a corresponding one of the two swinging units 44, and is located inside the liquid storage cavity, such that the stirring blade 56 can rotate coaxially with the swinging shaft 441 to stir the disinfectant inside the liquid storage cavity. The drug added to the disinfectant can be fully stirred and mixed with the disinfectant through stirring, thereby increasing a melting speed of the drug in the disinfectant. In an embodiment, the stirring blade 56 is arranged in plurality. The plurality of stirring blades 56 are sequentially arranged along the axial direction of the swinging shaft 441 of the corresponding one of the two swinging units 44, so as to improve the stirring effect when the disinfectant is stirred by the plurality of stirring blades 56.

In this embodiment, considering that in a case where the ground of the to-be-disinfected site is uneven, the disinfectant sprayed onto the ground by the spray nozzle 52 may accumulate, the disinfection robot is further provided with a liquid spreading mechanism 60. The disinfectant sprayed onto the ground by the spray nozzle 52 is spread flat by the liquid spreading mechanism 60, such that the disinfectant on the ground is distributed as evenly as possible. Specifically, referring to FIG. 2, The liquid spreading mechanism 60 includes a liquid spreading head 61, arranged at the second end of the swinging arm 41. A bottom of the liquid spreading head 61 is provided with a plurality of bristles contactable with the ground. When the swinging arm 41 swings reciprocatingly, the spray nozzle 52 and the liquid spreading head 61 can be driven by the swinging arm 41 to swing synchronously, such that the disinfectant is sprayed onto the ground by the reciprocatingly swinging spray nozzle 52. With the continuous movement of the disinfection robot, when the disinfection robot moves to the ground sprayed with the disinfectant, the disinfectant on the ground can be spread flat by the reciprocatingly swinging liquid spreading head 61 through the plurality of bristles, so as to avoid the accumulation of a large amount of disinfectant in a local area on the ground.

On the other hand, in order to further improve the effect of spreading the disinfectant by using the liquid spreading head 61 and the plurality of bristles, the liquid spreading mechanism 60 can further include a liquid spreading shaft 62, a liquid spreading gear 63 and a liquid spreading gear ring 64. Referring to FIG. 3, the liquid spreading head 61 is rotatably connected to the second end of the swinging arm 41 through the liquid spreading shaft 62, such that the liquid spreading head 61 is freely rotatable at the second end of the swinging arm 41. The liquid spreading gear 63 is sleevedly arranged on an outer wall of the liquid spreading shaft 62, and is coaxially arranged with the liquid spreading shaft 62, such that the liquid spreading gear 63 is coaxially rotatable with the liquid spreading shaft 62. The liquid spreading gear ring 64 has an arc-shaped structure, and is adapted to fit the swinging path of the swinging arm 41. The liquid spreading gear 63 is engaged with the liquid spreading gear ring 64. In an embodiment, the liquid spreading gear ring 64 is an incomplete outer gear ring, and is horizontally and fixedly arranged on an outer wall of the guard plate 30 close to the second end of the swinging arm 41.

In this way, when the swinging arm 41 swings reciprocatingly, the liquid spreading head 61, the liquid spreading shaft 62 and the liquid spreading gear 63 are synchronously driven by the swinging arm 41 to swing reciprocatingly. In this case, the liquid spreading gear 63 can perform reciprocating movements along a circumferential direction of the liquid spreading gear ring 64. At the same time, the liquid spreading gear 63 performs reciprocating rotation under the action of the liquid spreading ring gear 64 to drive the liquid spreading shaft 62 to rotate reciprocatingly. Furthermore, the liquid spreading head 61 is driven by the reciprocating rotating liquid spreading shaft 62 to rotate reciprocatingly, such that the disinfectant on the ground is spread flat by the rotating liquid spreading head 61 and the plurality of bristles. This facilitates the improvement of the effect of spreading the disinfectant using the liquid spreading head 61. Moreover, the disinfectant can be splashed to a farther area under the action of the plurality of bristles.

In order to more clearly and intuitively understand the disinfection robot provided herein, an operating principle of the disinfection robot will be further explained below.

In an initial stage, the swing amplitude of the swinging arm 41 is adjusted as needed to ensure excellent disinfection efficiency, that is, the rotating portion 4421 of each of the incomplete gears 442 is driven by a corresponding linear driver 443 to move along the axial direction of the swinging shaft 441, such that the tooth portions of the incomplete gears 442 of the two swinging units 44 with the same number of the teeth 4422a correspond to the swinging gear 43. For example, in a case of disinfecting a pedestrian walkway in a carriage, due to a relatively large width of the pedestrian walkway, an uppermost tooth portion 4422 can be configured to correspond to the swinging gear 43, which leads to a largest swing amplitude of the swinging arm 41. In a case of disinfecting a ground under seats, due to a relatively small width of the ground, a lowermost tooth portion 4422 can be configured to correspond to the swinging gear 43, which leads to a smallest swing amplitude of the swinging arm 41. At the same time, the disinfectant and the drug added into the liquid storage cavity.

During a disinfection stage, the driving motor 451 is started first, and the swinging shaft 441 of one of the two swinging units 44 is driven by the driving motor 451 to rotate, and the swinging shaft 441 of the other of the two swinging units 44 is driven to rotate in an opposite direction under the transmission action of the two transmitting gears 452. At this time, as the swinging shafts 441 of the two swinging units 44 continuously rotate in opposite directions, the swinging gear 43 can be driven by the incomplete gears 442 of the two swinging units 44 to rotate reciprocatingly within a certain angle range, such that the swinging arm 41 is driven by the swinging gear 43 and the hinge shaft 42 to swing reciprocatingly. In addition, the stirring blade 56 can be driven by the swinging shaft 441 extending into the liquid storage cavity to rotate to stir the disinfectant and drug in the liquid storage cavity to allow the two to be rapidly and fully mixed.

Subsequently, the disinfection robot moves along the ground of the to-be-disinfected site according to an instruction. For the first end of the swinging arm 41, the disinfectant in the liquid storage cavity that has been fully stirred and mixed is pumped into the spray nozzle 52 by the liquid pump 53 and then sprayed onto the ground by the spray nozzle 52, and the spray nozzle 52 is driven by the swinging arm 41 to swing reciprocatingly to increase a spraying area thereof, so as to achieve rapid disinfection of the ground of the disinfection site. For the second end of the swinging arm 41, the liquid spreading head 61, the liquid spreading shaft 62 and the liquid spreading gear 63 are driven by the swinging arm 41 to swing reciprocatingly and synchronously. The liquid spreading gear 63 is driven by the liquid spreading gear ring 64 to rotate reciprocatingly, such that the liquid spreading head 61 is driven by the liquid spreading gear 63 and the liquid spreading shaft 62 to rotate reciprocatingly. In this way, when the disinfection robot moves to the ground sprayed with the disinfectant, the disinfectant sprayed onto the ground by the spray nozzle 52 can be spread flat by the liquid spreading head 61 and the plurality of bristles, so as to avoid accumulation of a large amount of disinfectant in a local area on the ground.

Based on the prior art, by virtue of the structural improvement of the swinging mechanism 40, the disinfection robot provided therein can adjust the swing amplitude of the swinging arm 41 according to a size of the disinfection site, thereby adjusting a spraying range of the spray nozzle 52, so as to improve the practicality of the disinfection robot. This facilitates the use of the disinfection robot to disinfect various sizes of disinfection sites, resulting in better use effect and higher disinfection efficiency.

In addition, for the disinfection robot, a stirring blade 56 is provided on the swinging shaft 441 of one of the two swinging units 44, which is configured to stir the disinfectant and the drug in the liquid storage cavity, such that the disinfectant and the drug can be fully mixed, thereby further improving the disinfection effect. Moreover, a driving motor 451 is provided to simultaneously realize the swing of the swinging arm 41 and the rotation of the stirring blade 56, which leads to a more rational use of resources. The reciprocating swing of the swinging arm 41 can be realized by using an ordinary motor as the driving motor 451, without using a servo motor or a stepper motor with a higher cost.

Furthermore, the disinfection robot is provided with the liquid spreading mechanism 60, such that the liquid spreading head 61 the plurality of bristles thereof can be used to spread the disinfectant sprayed by the spray nozzle 52 onto the ground. This can effectively avoid the accumulation of a large amount of disinfectant in a local area on the ground, such that the disinfectant can be more evenly distributed on the ground of the disinfection site.

The embodiments described above are merely illustrative of the present disclosure, and are not intended to limit the scope of the present disclosure. It should be understood that various modifications, substitutions or improvements made by those of ordinary skill in the art without departing from the spirit of the present disclosure shall fall within the scope of the present disclosure defined by the appended claims.

What is claimed is:

1. A disinfection robot, comprising:
a top plate;
a bottom plate;
a swinging mechanism; and
a spraying mechanism;
wherein the top plate is located above the bottom plate; and the swinging mechanism is located between the top plate and the bottom plate;
the swinging mechanism comprises a swinging arm, a hinge shaft, a swinging gear, a first swinging unit, a second swinging unit and a driving unit;
the swinging arm has a first end and a second end;
the swinging arm is hingedly connected to the bottom plate through the hinge shaft with a hinge position located between the first end and the second end of the swinging arm;
the swinging gear is sleevedly arranged on an outer wall of the hinge shaft, and is coaxially arranged with the hinge shaft;
the first swinging unit is arranged at a first side of the swinging gear, and the second swinging unit is arranged at a second side of the swinging gear; the first swinging unit is symmetrically arranged with the second swinging unit; each of the first swinging unit and the second swinging unit comprises a swinging shaft, an incomplete gear and a linear driver; the swinging shaft is freely rotatable, and is vertically arranged; the incomplete gear comprises a rotating portion and a plurality of tooth portions; the rotating portion is sleevedly arranged on an outer wall of the swinging shaft, and is slidable along an axial direction of the swinging shaft; the plurality of tooth portions are sequentially arranged on a circumferential outer wall of the rotating portion from top to bottom; each of the plurality of tooth portions comprises a plurality of teeth sequentially provided along a circumferential direction of the rotating portion; the plurality of tooth portions vary in a number of the plurality of teeth, and are configured to be respectively engaged with the swinging gear; the linear driver is coaxially rotatable with the swinging shaft; and an output end of the linear driver is connected to the rotating portion to drive the rotating portion to slide along the axial direction of the swinging shaft;

the driving unit is configured to simultaneously drive the swinging shaft of the first swinging unit and the swinging shaft of the second swinging unit to rotate in opposite directions, such that the incomplete gear of the first swinging unit and the incomplete gear of the second swinging unit are alternately engaged with the swinging gear; and the spraying mechanism comprises a liquid storage tank having a liquid storage cavity, a spray nozzle and a liquid pump; the liquid storage tank is arranged on a top of the top plate; the spray nozzle is arranged at the first end of the swinging arm; an input end of the liquid pump is connected to the liquid storage cavity through a pipeline; and an output end of the liquid pump is connected to the spray nozzle through a hose.

2. The disinfection robot of claim 1, wherein the spraying mechanism further comprises a stirring blade; a top end of the swinging shaft of the first swinging unit passes through the top plate and the liquid storage tank in sequence to extend into the liquid storage cavity; and the stirring blade is arranged on the outer wall of the swinging shaft of the first swinging unit, and is located inside the liquid storage cavity.

3. The disinfection robot of claim 2, wherein the spraying mechanism further comprises a damping shaft; and the spray nozzle is rotatably connected to the first end of the swinging arm through the damping shaft.

4. The disinfection robot of claim 2, wherein a top of the liquid storage tank has an open structure, and is threadedly connected to a cover; and the stirring blade is configured as a plurality of stirring blades that are sequentially provided along the axial direction of the swinging shaft of the first swinging unit.

5. The disinfection robot of claim 1, wherein the driving unit comprises a driving motor and two transmitting gears;

the driving motor is arranged on the top plate; an output end of the driving motor is in transmission connection with the swinging shaft of one of the first swinging unit and the second swinging unit; and one of the two transmitting gears is sleevedly arranged on the outer wall of the swinging shaft of the first swinging unit, and is coaxially rotatable with the swinging shaft of the first swinging unit, and the other of the two transmitting gears is sleevedly arranged on the outer wall of the swinging shaft of the second swinging unit, and is coaxially rotatable with the swinging shaft of the second swinging unit; the two transmitting gears are engaged with each other.

6. The disinfection robot of claim 1, further comprising: a liquid spreading mechanism;

wherein the liquid spreading mechanism comprises a liquid spreading head arranged at the second end of the swinging arm; and a bottom of the liquid spreading head is provided with a plurality of bristles.

7. The disinfection robot of claim 6, wherein the liquid spreading mechanism further comprises a liquid spreading shaft, a liquid spreading gear and a liquid spreading gear ring;

the liquid spreading head is rotatably connected to the second end of the swinging arm through the liquid spreading shaft;

the liquid spreading gear is sleevedly arranged on an outer wall of the liquid spreading shaft, and is coaxially arranged with the liquid spreading shaft; and the liquid spreading gear ring has an arc-shaped structure, and is adapted to fit a swinging path of the swinging arm; and the liquid spreading gear is engaged with the liquid spreading gear ring.

8. The disinfection robot of claim 1, further comprising: a guard plate;

wherein the guard plate is arranged on a top of the bottom plate; an upper side of the guard plate is connected to the top plate; and a lower side of the guard plate is connected to the bottom plate; and the guard plate has an annular closed structure, and a space enclosed by the guard plate is configured as a protecting cavity; the swinging mechanism is located in the protecting cavity; two opposite sides of the guard plate are each provided with an avoidance opening; and the first end and the second end of the swinging arm extend outside the protecting cavity through the avoidance opening on each of the two opposite sides of the guard plate, respectively.

9. The disinfection robot of claim 1, wherein the hinge position is located at a center of the swinging arm.

10. The disinfection robot of claim 1, wherein two opposite sides of a top of the bottom plate are each provided with a sliding groove in an arc shape; two opposite sides of a bottom of the swinging arm are each provided with a sliding column fitting the sliding groove; one of sliding columns is located between the hinge shaft and the first end of the swinging arm; and the other of the sliding columns is located between the hinge shaft and the second end of the swinging arm.

\* \* \* \* \*